(12) United States Patent
Iijima et al.

(10) Patent No.: US 6,936,284 B2
(45) Date of Patent: Aug. 30, 2005

(54) COMPOSITION HAVING ANTICANCER ACTIVITY

(75) Inventors: Hideshi Iijima, Akishima (JP); Aizo Iijima, Kitasaitama-gun (JP)

(73) Assignee: Iijima Corporation, Tokyo (JP)

( * ) Notice: Subject to any disclaimer, the term of this patent is extended or adjusted under 35 U.S.C. 154(b) by 0 days.

(21) Appl. No.: 10/266,581

(22) Filed: Oct. 9, 2002

(65) Prior Publication Data

US 2003/0180318 A1 Sep. 25, 2003

(30) Foreign Application Priority Data

Nov. 16, 2001 (JP) ........................................ 2001-350954

(51) Int. Cl.$^7$ .............................................. A61K 35/78
(52) U.S. Cl. ........................ 424/729; 424/725; 424/581
(58) Field of Search ................................ 424/581, 729, 424/725

(56) References Cited

U.S. PATENT DOCUMENTS

6,168,795 B1 * 1/2001 DJang
6,720,010 B2 * 4/2004 Iijima et al.

FOREIGN PATENT DOCUMENTS

| JP | 02149525 A | * | 6/1990 |
| JP | 04029968 A | * | 1/1992 |
| JP | 6-72885 A | * | 3/1994 |
| JP | 6-1281168 A | * | 5/1994 |

OTHER PUBLICATIONS http://plants.usda.gov/cgi_bin/plant_profile.cgi?symbol=CAMEL2.*

CAPLUS abstract of KR 9606573 B1 (1996).*

S. Valcic, et al., Anti–Cancer Drugs, vol. 7, No. 4, pp. 461–468, XP–001010512, "Inhibitory Effect of Six Green Tea Catechins and Caffeine on the Growth of Four Selected Human Tumor Cell Lines", 1996.

T. Okuyama, et al., Database Biosis Online!, Biosciences Information Service, vol. 57, No. 3, 1 page, XP–002230247, "Anti–Tumor–Promotion by Priniciples Obtained From Angelica–Keiskei", 1991.

T, Okuyama, et al., Database Biosis Online!, Biosciences Information, vol. 38, No. 4, 1 page, XP–002230248, "Studies on the Antitumor–Promoting Activity of Naturally Occuring Substances II. Inhibition of Tumor–Promoter–Enhanced Phospholipid Metabolism by Umbelliferous Materials", 1990.

G. J. Hammons, et al., Database Biosis Online!. Biosciences Information Services, vol. 33, No. 1, 2 pages, XP–0022303249,, "Effects of Chemoprotective Agents on the Metabolic Activation of the Carcinogenic Arylamines PhIP and 4–Aminobiphenyl in Human and Rat Liver Microsomes", 1999.

* cited by examiner

*Primary Examiner*—Susan D. Coe
(74) *Attorney, Agent, or Firm*—Oblon, Spivak, McClelland, Maier & Neustadt, P.C.

(57) ABSTRACT

To conduct a search for natural drugs and their formulae derived from natural substances that hardly cause side effects and drug tolerance, based on quite a new idea having departed from conventional drugs such as Chinese galenicals, Chinese medicine formulae, etc. and to develop a composition that has an anticancer activity and is selectively cytotoxic to cancer cells. A composition having an anticancer effect is obtained, which comprises therapeutically effective amounts of a dry product of *Angelica keiskei* and a dry product of *Theaceae Camellia*. Also, a composition having an anticancer activity is obtained, which comprises therapeutically effective amounts of a dry product of *Angelica keiskei* and/or a dry product of *Theaceae Camellia* together with a dry product of defatted whole egg of eggs of a fowl bred by feeding a feed having blended therein an additive comprising a dry product of *Angelica keiskei*, a dry product of brown algae, and optionally a dry product of *Theaceae Camellia*.

12 Claims, No Drawings

# COMPOSITION HAVING ANTICANCER ACTIVITY

FIELD OF THE INVENTION

The present invention relates to a composition having an anticancer activity containing components derived from natural substances as active components and more particularly to a composition having anticancer activity containing dry products of certain plants.

BACKGROUND OF THE INVENTION

Natural substances are known to contain components useful as drugs, such as anticancer agents and many drugs have been thus far developed from natural substances. Typical examples of anticancer agents derived from natural substances developed in recent years and now clinically put into practical use include irinotecan hydrochloride (CPT-11) semi-synthesized from camptothecin, which is an extracted alkaloid from Camptotheca trees from china, taxotere (TXT) semi-synthesized from extracts of the needles of Western yew trees (*Taxus brevifolia*), taxol (TXL) isolated from extracts of the bark of Pacific yew trees, etc.

The anticancer agents derived from natural substances like the anticancer agents whose active components are synthetic compounds, are strongly injurious (or toxic) to cancer cells thus they have also strong affects on normal cells, and may induce severe side effects, resulting in many cases in abandonment of the therapy by medication.

Also, in the midway of the therapy by medication, there arises in many clinical sites a problem of drug tolerance that cancer cells acquire in which the drug or other plural drugs will become no longer effective. This is a great hindrance to the therapy by medication.

On the other hand, Chinese medicine formulae prepared by blending a plurality of galenicals containing many active components have advantages in that they exhibit gentle and sustained effects and that they hardly cause side effects and drug tolerance. However, since they can give no sufficient effects, there have been substantially no cases in which they are used for the purpose of treating cancers.

Under the circumstances, there exists a possibility that search on natural substances of animal and plant origin will result in finding ones including active anticancer components. Actually, many such approaches have been proposed in patent information, academic literature, etc.

However, the conventional methods in which an anticancer component alone is isolated and purified or semi-synthesized from a particular natural substance as a therapeutic drug cannot solve the problems of side effects and drug tolerance, which are the biggest problems of cancer therapy. So far as the organism recognizes an anticancer agent as a foreign matter containing a cytotoxic factor, the problems of side effects and drug tolerance cannot be avoided to occur. Furthermore, other problems on anticancer agents derived from natural substances include one that in many cases the component found with difficulty is poor as a resource, so that its industrial application is impossible.

SUMMARY OF THE INVENTION

Therefore, an object of the present invention is to conduct a search for natural drugs and their formulae derived from natural substances that hardly cause side effects and drug tolerance, based on quite a new idea having departed from conventional drugs such as Chinese galenicals, Chinese medicine formulae, etc. and develop a composition that has an anticancer activity and is selectively cytotoxic to cancer cells.

We, inventors of the present invention have made extensive studies with a view to solving the above-mentioned problems and as a result they have found that blending a dry product of *Angelica keiskei* ("Ashitaba", in Japanese) and a dry product of *Theaceae Camellia* ("Tsubaki", in Japanese) can give rise to a composition having excellent anticancer activity without causing any side effects. Furthermore, they have also found that a composition containing a blend of the above-mentioned dry product of *Angelica keiskei* (hereinafter referred to as "*Angelica keiskei* dry product") and/or the dry product of *Theaceae Camellia* (hereinafter referred to as "*Theaceae Camellia* dry product") with a dry product of defatted whole egg (hereinafter referred to as "defatted whole egg dry product") of eggs produced by fowls fed with a feed containing such a dry product or products has anticancer activity. That is, we have found that a composition containing an *Angelica keiskei* dry product and a *Theaceae Camellia* dry product gives no adverse influence on normal cells but is cytotoxic exclusively to cancer cells to inhibit their growth. They have also found that a composition containing the above-mentioned defatted whole egg dry product and the *Angelica keiskei* dry product and/or the *Theaceae Camellia* dry product has an anticancer activity.

The present invention has been accomplished based on these findings.

According to a first aspect of the present invention, the present invention relates to a composition having an anticancer activity, characterized by comprising therapeutically effective amounts of a dry product of *Angelica keiskei* and a dry product of *Theaceae Camellia*.

According to a second aspect of the present invention, the present invention relates to a composition having an anticancer activity, characterized by comprising therapeutically effective amounts of a dry product of *Angelica keiskei* and/or a dry product of *Theaceae Camellia*, and a dry product of defatted whole egg of eggs of a fowl bred by feeding a feed having blended therein an additive comprising a dry product of *Angelica keiskei*, a dry product of brown algae, and optionally a dry product of *Theaceae Camellia*.

According a third aspect of the present invention, the present invention relates to a composition according to the second aspect of the invention, wherein the fowl is a member selected from the group consisting of hens, ducks and quails.

According to the present invention, novel natural drugs derived from natural substances departing from conventional drugs such as Chinese galenicals, Chinese medicine formulae, etc. are provided. That is, compositions that contain components derived from natural substances as active components and have anticancer activity, i.e., selective toxicity to cancer cells are provided. In particular, the compositions of the present invention are excellent in specific anticancer effect to leukemia cells.

In addition, the compositions of the present invention are extremely weak in toxicity so that it is expected that they can be utilized not only in the therapy of cancers, etc. as drugs but also in preventing the above-mentioned diseases by adding them to various foods and making it possible to take them daily.

DETAILED DESCRIPTION OF THE INVENTION

As described above, the present invention relates to composition having anticancer activity derived from familiar products that have never been used conventionally as raw materials, such as *Angelica keiskei* and *Theaceae Camellia*, which are natural substances, as well as a dry product of whole egg defatted from specified eggs produced by utilizing such natural substances as feeds.

Although it is unclear as to what compound contained in the components constituting the composition of the present invention is the main body that exhibits pharmacological activity, it is believed that a plurality of compounds contained therein act in combination with each other.

*Angelica keiskei* (Ashitaba) used as a raw material in the present invention is an umbelliferous perennial plant known to have strong authigenic ability and contain abundant nutritional components. It is authigenically distributed mainly in the southern coasts of Izu peninsula and Izu islands, Japan. However, recently it is also cultivated as a vegetable or the like in Japan.

Various portions, such as leaves, stems, and roots, of *Angelica keiskei* maybe used, with leaves and stems being preferred. However, there has been no report on utilization of *Angelica keiskei* as a component of a drug having anticancer activity.

The *Angelica keiskei* dry product used in the present invention can be obtained, for example, by cutting *Angelica keiskei* to a suitable size (usually 10 to 15 mm square) after optionally washing the leaves and stems of *Angelica keiskei* with water, freezing the cut plant pieces, and then sublimating the iced water in vacuum to dry them. The dry product is used usually after it is processed into the form of powder in consideration of convenience. This is yellowish green (young leaf color) powder. Hereinafter, the *Angelica keiskei* dry product is referred to as "I-01B".

*Theaceae Camellia* (Tsubaki) is an evergreen tall tree that is authigenically distributed in Honshu, Shikoku, Kyushu, etc. districts in Japan and includes many kinds of variations for appreciation, etc. prepared by breeding. In the present invention, a wild type of *Camellia japonica* (Yabutsubaki) is preferable.

The portions of *Theaceae Camellia* to be used in the present invention include leaves, flowers, seeds, etc., with leaves being particularly preferable. Thus far no report has been made on utilization of leaves, etc. of *Theaceae Camellia* as components of drugs. In the present invention, the *Theaceae Camellia* dry product obtained by roasting, for example, leaves, etc. of *Theaceae Camellia* are used as the *Theaceae Camellia* dry product. This can be obtained as follows. First, picked *Theaceae Camellia* leaves are dried. The drying is performed by heating them at 60 to 80° C. for 3 to 5 hours. Then, the dry product is cut to a suitable size (usually, about 5 mm square) and then roasted. The roasting is performed generally by using a hot iron plate drum type roasting apparatus at 100 to 150° C. for 10 to 30 minutes. For the same reason as in the case of the dry product of *Angelica keiskei*, usually powdered *Theaceae Camellia* is used. This is brown powder. Hereinafter, the *Theaceae Camellia* dry product is referred to as "I-01C".

The eggs produced by fowls to be used in the present invention are those eggs produced by fowls bred (or raised) by feeding with a feed comprising an additive including I-01B and a dry product of brown algae (hereinafter referred to as "brown algae dry product"), for example, dried tangle weed, as an auxiliary component, or a feed comprising an additive containing I-01B, I-01C and the brown algae dry product. Note that as basal feeds, those feeds commonly used in breeding fowls are used. For preparing feed additives, respective raw materials are blended in the following ratios: (1) I-01B:brown algae dry product=1-4:1-4 (by weight ratio), preferably 1:1 (by weight ratio), or (2) I-01B:I-01C:brown algae dry product=1-4:1-4:1-4 (by weight ratio), preferably 2:1:1 (by weight ratio).

The blending amounts of the additives to the feed are not particularly limited but in the case of the additive (1), the blending amount of the additive is 1 to 20% by weight, preferably 2 to 8% by weight while in the case of the additive (2), the blending amount of the additive is 1 to 20% by weight, preferably 2 to 8% by weight.

Fowls may be bred by a conventional method except that the special additives as described above are blended to the feed. The fowls include hens, ducks, quails, etc., with hens being preferable.

Eggs must be collected after at least 10 days' feeding on a feed having blended therein the above-mentioned additives. Generally, the period during which the components contained in the feed additive move over into eggs is considered to be about 3 days in the case of water-soluble components and about 3 weeks in the case of fat-soluble components. However, according to the finding by the inventors of the present invention, a conclusion has been obtained that it is desirable that egg collection is done after feeding the feed containing the above-mentioned additive to the fowls for at least 10 days.

Although details are unclear, the inventors of the present invention have also found that protein in the above-mentioned eggs is useful for the purpose of the present invention.

Accordingly, the whole egg of the collected eggs is, after defatting, dried to obtain a dry product. That is, liquid egg obtained by cracking eggs is sufficiently agitated to homogenize it and then frozen by a conventional method to obtain frozen whole egg, which then is dried. The drying is performed preferably by using a microwave drier under controlling the power and heating time of the microwave drier so that the temperature of the product does not exceed a range of 80 to 90° C. This can provide a whole egg dry product in the form of chips.

Then, the whole egg dry chips are defatted by extracting them by distillation with an alcohol such as methanol, ethanol, etc., as an extraction solvent, and thereafter, the defatted whole egg is recovered. Note that at the time of extraction, the solvent is heated to a temperature not higher than 60° C. and the extraction is completed within 1.5 hours, preferably in from 30 minutes to 1 hour. If necessary, this defatting treatment may be repeated several times.

By applying a hot air drying to the defatted whole egg, a whole egg dry product is obtained. Note that it is preferred that the hot air drying is performed by using a hot air fluidized bed type drier or the like. Since powder is desirable also in the case of whole egg dry product, usually powdered whole egg dry product is used. This can be obtained by pulverizing the whole egg dry product to a suitable size by using, for example, a pulverizer such as a hammer mill. The whole egg dry product thus obtained has a pale brown color. The defatted whole egg dry product derived from eggs obtained by breeding fowls with a feed having blended therein the additive (1) is referred to as "I-01A(1)", and the defatted whole egg dry product derived from eggs obtained by breeding the fowls with a feed having blended therein the additive (2) is referred to as "I-01A(2)".

The composition containing I-01B, which is the above-mentioned *Angelica keiskei* dry product, and I-01C, which is the above-mentioned *Theaceae Camellia* dry product, as active components is the composition having anticancer activity according to the first aspect of the present invention.

Also, the composition containing I-01A, which is the above-mentioned defatted whole egg dry product, specifically I-01A(1) or I-01A(2), together with I-01B, which is the above-mentioned *Angelica keiskei* dry product, and/or I-01C, which is the above-mentioned *Theaceae Camellia* dry product, as active components is the composition having anticancer activity according to the second aspect of the present invention.

The drug compositions of the present invention are very low in toxicity. For example, in a repetitive administration of mixed feed in which a composition containing I-01A and I-01B in combination is administered to rats for 2 weeks at a mixed ratio of 30%, no toxicity was observed.

In the case of other compositions containing other combinations, in mouse leukemia pharmacological experiments conducted by administration at a mixed ratio of 20 to 45%, there has been observed no change suggesting toxicity in general states such as body weight, feed taking amount, amount of exercise, etc. throughout the period of 10 days before transplantation of leukemia cells and survival period after the transplantation as compared to the non-administered control group. In addition, they exhibited significant anticancer effect of 200% or more in terms of life extension ratio.

Therefore, the drug compositions of the present invention are excellent in safety and can be used as food additives so that daily uptake thereof can prevent diseases.

The drug compositions of the present invention are administered mainly by an oral route. The form of the compositions is not particularly limited and they can be prepared into capsules, granules, tablets, etc. by, for example, a conventional preparation method.

The dosages and blending ratios of the respective components when the drug compositions of the present invention are used for humans are as follows. In the case of the composition according to the first aspect of invention, it is suitable to administer the composition in a blending ratio of I-01B:I-01C=1-10:1-10, preferably I-01B:I-01C=1-2:1-2 at a dosage of 0.2 to 20 g/day, preferably 1 to 5 g/day. In the case of the composition according to the second aspect of the invention, it is suitable to administer the composition in a blending ratio of 1-01A:I-01B or I-01C=1-10:0.5-5, preferably I-01A:I-01B or I-01C=1-2:0.5-1, at a dosage of 0.2 to 20 g/day, preferably 1 to 5 g/day. Also, in the case of the composition having a formulation of I-01A, I-01B and I-01C, it is suitable to administer the composition in a blending ratio of I-01A:I-01B:I-01C=1-10:0.5-5:0.5-5, preferably I-01A:I-01B:I-01C=1-2:0.5-1:0.5-1 at a dosage of 0.2 to 20 g/day, preferably 1 to 5 g/day.

The blending ratios and dosages of the respective components described above are merely exemplary and since the components are not toxic, the blending ratios and dosages are not particularly limited to the above-mentioned values and various preparations and formula patterns of dosage in consideration of conditions such as site of disease, progress of disease, state of disease, sex, age, etc. as appropriate are applicable.

Furthermore, also when the drug compositions of the present invention are used as food additives, there is no fear of any toxicity or side effects, so that the addition amounts to foods, etc. may be determined in consideration of the above-mentioned preparations and formula patterns of dosage, etc.

EXAMPLES

Hereinafter, the present invention will be described in detail by examples. However, the present invention should not be considered as being limited thereto.

Production Example 1
Production of Ashitaba Dry Product
(1) Leaves and stems of *Angelica keiskei* (Ashitaba) were cut from cultivation field of *Angelica keiskei* to obtain 1,960 kg of a raw material. The length of the obtained stems was adjusted to 70 to 80 cm. Then, the raw material was washed with tap water. The component analysis of (raw) leaves of *Angelica keiskei* gave results as shown in Table 1.

The washed raw material was cut to about 10 to 15 mm square with a cutter.
(2) The cut raw material was placed on a tray and preliminarily frozen. Furthermore, after freezing the cut raw material in a freeze-drier, the freeze-drier was evacuated to sublimate the frozen water.

The obtained freeze-dried product was pulverized in a pulverizer to a size of about 100 meshes. Thus, 238.5 kg of *Angelica keiskei* dry product powder I-01B was obtained.

TABLE 1

| General Components Composition | |
|---|---|
| Item | Content* |
| Water | 88.6 g |
| Protein | 3.3 g |
| Lipids | 0.1 g |
| Ash | 1.3 g |
| Carbohydrates (sugars) | 5.2 g |
| Carbohydrates (fibers) | 1.5 g |
| Energy | 33 kcal |
| Sodium | 60 mg |
| Potassium | 540 mg |
| Substantial amount of salt | 0.2 g |

*Quoted from "Fourth Edition, Japan Standard Tables of Food Composition (1982)"

Production Example 2
Production of *Camellia* Dry Product
(1) Raw leaves of *Camellia japonica* (Yabutsubaki, wild type) were picked to obtain 476 kg of a raw material. The raw material was washed with tap water. Then, the raw material was heated at 70° C. for 5 hours to obtain a dry product, which then was roasted on a hot iron plate at 135° C. for 15 minutes to obtain a roasted dry product.
(2) The above-mentioned roasted dry product was pulverized by a pulverizer to a size of about 30 meshes to obtain 116.7 kg of *Theaceae Camellia* dry product powder I-01C.

The component analysis of the *Theaceae Camellia* dry product powder I-01C was performed. That is, general components composition, amino acid composition and fatty acid composition in 100 g of edible portion were examined. The results obtained are shown in Tables 2, 3, and 4, respectively.

TABLE 2

| General Components Composition | |
|---|---|
| Item | Content |
| Water | 5.4 g |
| Protein | 9.0 g |
| Lipids | 3.9 g |
| Ash | 5.9 g |
| Carbohydrates | 75.6 g |
| Energy | 374 kcal |
| Sodium | 129 mg |
| Substantial amount of salt | 0.3 g |
| Tannic acid | 5200 mg |

TABLE 3

Amino Acid Composition

| Item | Content (mg) |
|---|---|
| Arginine | 356 |
| Lysine | 414 |
| Histidine | 163 |
| Phenylalanine | 399 |
| Tyrosine | 226 |
| Leucine | 668 |
| Isoleucine | 298 |
| Methionine | 48 |
| Valine | 384 |
| Alanine | 456 |
| Glycine | 470 |
| Proline | 392 |
| Glutamic acid | 858 |
| Serine | 387 |
| Threonine | 357 |
| Aspartic acid | 626 |
| Cystine | 7 |
| Hydroxyproline | 94 |
| γ-aminobutric acid | 52 |

TABLE 4

Fatty Acid Composition

| Item | Content (g) |
|---|---|
| Palmitic acid | 0.30 |
| Palmitoleic acid | 0.06 |
| Stearic acid | 0.03 |
| Oleic acid | 0.10 |
| Linoleic acid | 0.08 |
| Linolenic acid | 0.20 |

Production Example 3

Production of Egg (Part 1)

(1) Preparation of Feed Additive

The *Angelica keiskei* dry product I-01B obtained in Production Example 1 and commercially available cut tangle weed (dry product) were mixed in a weight ratio of 1:1 to prepare a feed additive.

(2) Preparation of Feed

To a basal feed (trade name: Kumiai Blended Feed for Adult Chicken SELECT, produced by Asahi Industries Co., Ltd.; composition, 61% of grains, 20% of plant oil cakes, 5% of animal-derived feed, 4% of chaff and bran, 10% of miscellaneous) was blended 2% by weight of the feed additive obtained as described in (1) above to prepare a feed.

(3) Feeding and Egg Collection

A thousand (1,000) egg-laying hens which were all 300 days old were given the feed as described in (2) above and allowed to freely take it. Egg-laying ratio was good and no difference in egg-laying ratio from that of normal egg-laying hens fed under the same conditions was observed. After 10 days from the start of feeding, eggs were continuously collected for 23 days to obtain 1,200 kg of eggs.

(4) Component analysis of the egg obtained as described in (3) above was performed. That is, the general components composition and amino acid composition in 100 g of edible portion were examined. The results obtained are shown in Tables 5 and 6, respectively.

TABLE 5

General Components Composition

| Item | Egg of the present invention | Control egg* |
|---|---|---|
| Water | 74.9 g | 74.7 g |
| Protein | 12.8 g | 12.3 g |
| Lipids | 10.1 g | 11.2 g |
| Ash | 1.0 g | 0.9 g |
| Carbohydrates | 1.2 g | 0.9 g |
| Energy | 147 kcal | 162 kcal |
| Sodium | 147 mg | 130 mg |
| Cholesterol | 471 mg | 470 mg |
| Iodine | 0.4 mg | (0.02 mg)** |

*Quoted from "Fourth Edition, Japan Standard Tables of Food Composition (1982)"
**Calculated value

TABLE 6

Amino acid Composition (content in grams)

| Item | Egg of the present invention | Control egg* | Item | Egg of the present invention | Control egg* |
|---|---|---|---|---|---|
| Arginine | 0.84 | 0.78 | Alanine | 0.74 | 0.70 |
| Lysine | 0.97 | 0.89 | Glycine | 0.44 | 0.41 |
| Histidine | 0.34 | 0.31 | Proline | 0.49 | 0.47 |
| Phenylalanine | 0.72 | 0.64 | Glutamic acid | 1.71 | 1.60 |
| Tyrosine | 0.58 | 0.50 | Serine | 0.99 | 0.84 |
| Leucine | 1.15 | 1.10 | Threonine | 0.63 | 0.57 |
| Isoleucine | 0.69 | 0.68 | Aspartic acid | 1.34 | 1.30 |
| Methionine | 0.46 | 0.40 | Tryptophan | 0.19 | 0.19 |
| Valine | 0.86 | 0.83 | Cystine | 0.36 | 0.32 |

*Quoted from "Revised Japan standard Tables of Food Composition (1986)"

Production Example 4

Production of Egg (Part 2)

(1) Preparation of Feed Additive

The *Angelica keiskei* dry product I-01B obtained in Production Example 1, the *Theaceae Camellia* dry product I-01C obtained in Production Example 2, and commercially available cut tangle weed (dry product) were mixed in a weight ratio of 2:1:1 to obtain a feed additive.

(2) Preparation of Feed

To a basal feed (trade name: Kumiai Blended Feed for Adult Chicken SELECT, produced by Asahi Industries Co., Ltd.; composition, 61% of grains, 20% of plant oil cake, 5% of animal-derived feed, 4% of chaff and bran, 10% of miscellaneous) was blended 8% by weight of the feed additive obtained as described in (1) above to prepare a feed.

(3) Feeding and Egg Collection

Seven hundred (700) egg-laying hens which were all 180 days old were given the feed as described in (2) above and allowed to freely take it. Egg-laying ratio was good and no difference in egg-laying ratio from that of normal egg-laying hens fed under the same conditions was observed. After 10 days from the start of feeding, eggs were collected continuously for 35 days to obtain 1,150 kg of eggs.

(4) Component analysis of the egg obtained as described in (3) above was performed. That is, the general components composition and amino acid composition in 100 g of edible portion were examined. The results obtained are shown in Tables 7 and 8, respectively.

TABLE 7

General Components Composition

| Item | Egg of the present invention | Control Egg * |
|---|---|---|
| Water | 75.6 g | 74.7 g |
| Protein | 13.2 g | 12.3 g |
| Lipids | 8.6 g | 11.2 g |
| Ash | 0.8 g | 0.9 g |
| Carbohydrates | 1.8 g | 0.9 g |
| Energy | 137 kcal | 162 kcal |
| Sodium | 132 mg | 130 mg |
| Cholesterol | 412 mg | 470 mg |
| Iodine | 0.18 mg | (0.02 mg) ** |

* Quoted from "Fourth Edition, Japan Standard Tables of Food Composition (1982)"
** Calculated value

TABLE 8

Amino Acid Composition (content in grams)

| Item | Egg of the present invention | Control egg* | Item | Egg of the present invention | Control egg* |
|---|---|---|---|---|---|
| Arginine | 0.86 | 0.78 | Alanine | 0.78 | 0.70 |
| Lysine | 0.97 | 0.89 | Glycine | 0.49 | 0.41 |
| Histidine | 0.30 | 0.31 | Proline | 0.50 | 0.47 |
| Phenylalanine | 0.73 | 0.64 | Glutamic acid | 1.78 | 1.60 |
| Tyrosine | 0.50 | 0.50 | Serine | 0.96 | 0.84 |
| Leucine | 1.14 | 1.10 | Threonine | 0.57 | 0.57 |
| Isoleucine | 0.56 | 0.68 | Aspartic Acid | 0.99 | 1.30 |
| Methionine | 0.43 | 0.40 | Tryptophan | 0.08 | 0.19 |
| Valine | 0.70 | 0.83 | Cystine | 0.26 | 0.32 |

*Quoted from "Revised Japan Standard Tables of Food Composition (1986)"

Production Example 5
Production of Defatted Whole Egg Dry Product (Part 1)
(1) Freezing of Whole Egg
1,160 kg of whole egg obtained in Production Example 3 was cracked, and thus obtained liquid whole egg was sufficiently agitated and then frozen to obtain 938.9 kg of frozen whole egg.
(2) Drying Treatment
The frozen whole egg as described in (1) above was dried by microwave to obtain dry whole egg chips. When performing the drying, the temperature of the product was controlled so as to be kept at no higher than 90° C.
(3) Defatting Treatment
The dry whole egg chips as described in (2) above were refluxed with ethanol heated at 60° C. to extract lipids. The extraction time for lipids was set to 1 hour per time and the defatting was performed 2 times. Thereafter, the solvent and lipids were recovered by distillation to obtain the objective defatted extract.
(4) Drying Treatment
The defatted extract obtained as described in (3) above was subjected to hot air drying with a hot air fluidized bed type drier to obtain a defatted whole egg dry product.
(5) Pulverizing Treatment
The defatted whole egg dry product obtained as described in (4) above was pulverized to a size of about 100 meshes by using a hammer mill to obtain 111.3 kg of the objective defatted whole egg dry product powder I-01A(1).
(6) Component analysis of the defatted whole egg dry product powder I-01A(1) obtained as described in (5) above was performed. That is, the general components composition and amino acid composition in 100 g of edible portion were examined. The results obtained are shown in Tables 9 and 10, respectively.

TABLE 9

General Components Composition

| Item | I-01A(1) | Control dried whole egg* |
|---|---|---|
| Water | 5.4 g | 3.2 g |
| Protein | 86.9 g | 47.2 g |
| Lipids | 0.8 g | 41.7 g |
| Ash | 3.6 g | 3.8 g |
| Carbohydrates | 3.3 g | 4.1 g |
| Energy | 366 kcal | 611 kcal |
| Sodium | 569 mg | 500 mg |
| Substantial amount of salt | 1.4 g | 1.3 g |

*Quoted from "Fourth Edition, Japan Standard Tables of Food Composition (1982)"

TABLE 10

Amino Acid Composition (content in milligrams)

| Item | I-01A(1) | Item | I-01A(1) |
|---|---|---|---|
| Arginine | 4774 | Alanine | 4626 |
| Lysine | 4955 | Glycine | 2832 |
| Histidine | 1808 | Proline | 2903 |
| Phenylalanine | 4086 | Glutamic acid | 11172 |
| Tyrosine | 2895 | Serine | 6422 |
| Leucine | 6762 | Threonine | 3797 |
| Isoleucine | 3585 | Aspartic acid | 8416 |
| Methionine | 2499 | Tryptophan | 51 |
| Valine | 4410 | Cystine | 1549 |

Production Example 6
Production of Defatted Whole Egg Dry Product (Part 2)
(1) Freezing of Whole Egg
1,090 kg of whole egg obtained in Production Example 4 was cracked, and thus obtained liquid whole egg was sufficiently agitated and then frozen to obtain 890 kg of frozen whole egg.
(2) Drying Treatment
The frozen whole egg as described in (1) above was dried by microwave to obtain dry whole egg chips. When performing the drying, the temperature of the product was controlled so as to be kept at no higher than 90° C.
(3) Defatting Treatment
The dry whole egg chips as described in (2) above were refluxed with ethanol heated at 60° C. to extract lipids. The extraction time for lipids was set to 1 hour per time and the defatting was performed 2 times. Thereafter, the solvent and lipids were recovered by distillation to obtain the objective defatted extract.
(4) Drying Treatment
The defatted extract obtained as described in (3) above was subjected to hot air drying with a hot air fluidized bed type drier to obtain a defatted whole egg dry product.
(5) Pulverizing Treatment
The defatted whole egg dry product obtained as described in (4) above was pulverized to a size of about 100 meshes by using a hammer mill to obtain 104.38 kg of the objective defatted whole egg dry product powder I-01A(2).
(6) Component analysis of the defatted whole egg dry product powder I-01A(2) obtained as described in (5) above was performed. That is, the general components composition and amino acid composition in 100 g of edible portion were examined. The results obtained are shown in Tables 11 and 12, respectively.

TABLE 11

General Components Composition

| Item | I-01A(2) | Control dried whole egg* |
|---|---|---|
| Water | 5.3 g | 3.2 g |
| Protein | 82.7 g | 47.2 g |
| Lipids | 3.5 g | 41.7 g |
| Ash | 3.8 g | 3.8 g |
| Carbohydrates | 4.7 g | 4.1 g |
| Energy | 381 kcal | 611 kcal |
| Sodium | 685 mg | 500 mg |
| Substantial amount of salt | 1.7 g | 1.3 g |

*Quoted from "Fourth Edition, Japan Standard Tables of Food Composition (1982)"

TABLE 12

Amino Acid Composition (content in milligrams)

| Item | I-01A(2) | Item | I-01A(2) |
|---|---|---|---|
| Arginine | 4672 | Alanine | 4536 |
| Lysine | 4813 | Glycine | 2773 |
| Histidine | 1868 | Proline | 2811 |
| Phenylalanine | 3981 | Glutamic acid | 10860 |
| Tyrosine | 2670 | Serine | 6215 |
| Leucine | 6571 | Threonine | 3699 |
| Isoleucine | 3512 | Aspartic acid | 8218 |
| Methionine | 2295 | Tryptophan | 63 |
| Valine | 4280 | Cystine | 1541 |

Example 1

Using a composition I-01A(1):I-01B composed of a mixture of the defatted whole egg dry product powder I-01A(1) as obtained in Production Example 5 and the *Angelica keiskei* dry product I-01B as obtained in Production Example 1 as a test substance, anticancer effect of the composition against ascites tumor caused by transplanting a leukemia cell, Leukemia L-1210, to mice was tested.

As the laboratory animal species/phyletic line, Cri:CDF mice (5 weeks old) were used.

As the test substance, a feed having blended therein a composition of 11:4 (weight ratio) of the defatted whole egg dry product powder I-01A(1) and the *Angelica keiskei* dry product I-01B was prepared and orally administered to mice. Note that the feed was prepared by blending a powder feed (trade name: CDE-2, produced by CLEA Japan, Inc.) as a basal feed with the above-mentioned composition at a mixing ratio of 28%, 36% or 44%, and the animals were allowed to orally and freely take said feed.

The number of days of administration was set to 10 days before the transplantation of Leukemia L-1210 and the survival period after the transplantation. The test groups were 3 groups having the above-mentioned different mixing ratios, and 1 group was a control group in which no test substance was administered. Note that in practicing the test, the number of animals was 8 in each group.

Leukemia cells Leukemia L-1210 were prepared as follows. That is, a cell suspension of L-1210 in physiological saline to a cell density of 1×10⁶ cell/ml was prepared and 0.1 ml of the suspension was transplanted in the abdominal cavity of a mouse to make an ascites tumor mouse model. The transplantation was made on Day 11 from the administration of the test substance.

The test of anticancer effect was performed by measuring the survival period of each group and calculating life extension ratio (T/C %) expressed by the following equation assuming the survival period of the control group as 100%.

[Equation 1]

Life extension ratio={(Average number of days of survival of the test substance-administered group)/(Average number of days of survival of the control group)}×100

TABLE 13

Anticancer Effect

| Classification | | Average number of days of survival | Life extension ratio (%) |
|---|---|---|---|
| Control group | | 13 | 100 |
| I-01A (1): I-01B-administered group | 28% feed mixing ratio | 14 | 107.7 |
| | 36% feed mixing ratio | 16 | 123.1 |
| | 44% feed mixing ratio | 17 | 130.8 |

Example 2

Various compositions obtained by combining and mixing the defatted whole egg dry product powder I-01A(2) as obtained in Production Example 6 and the *Angelica keiskei* dry product I-01B as obtained in Production Example 1 and the *Theaceae Camellia* dry product I-01C as obtained in Production Example 2, i.e., I-01A(2):I-01B, I-01A(2):I-01C, I-01B:I-01C, and I-01A(2):I-01B:I-01C were each used as test substances. Each of them was tested on the anticancer effect against ascites tumor developed in a mouse by transplanting leukemia cell, Leukemia L-1210 thereto.

As the laboratory animal species/phyletic line, Cri:CDF mice (5 weeks old) were used.

As for the preparation of the test substances, a composition of I-01A(2):I-01B=70:30 (weight ratio), a composition of I-01A(2):I-01C=70:3 (weight ratio), a composition of I-01B:I-01C=35:3 (weight ratio), and a composition of I-01A(2):I-01B:I-01C=65:35:3 (weight ratio) were each mixed with a feed and orally administered. The oral administration was performed by free feeding. The feed was prepared by mixing a powder feed (trade name: CRF, produced by Oriental Yeast Industry Co., Ltd.) as a basal feed with each of the above-mentioned compositions at a predetermined mixing ratio.

The number of days of administration was set to 10 days before the transplantation of Leukemia L-1210 and the survival period after the transplantation. The test groups were 9 groups to which the above-mentioned four compositions were administered with different mixing ratios, and one group was a control group to which no test substance was administered. Note that in practicing the test, the number of animals was 8 in each group.

Leukemia cells, Leukemia L-1210, were prepared as follows. That is, a cell suspension of L-1210 in physiological saline to have a cell density of 1×10⁶ cell/ml was prepared and 0.2 ml of the suspension was transplanted in the abdominal cavity of a mouse to make an ascites tumor mouse model. The transplantation was made on Day 11 from the administration of the test substance.

The test of anticancer effect was performed by measuring the survival period of each group and calculating life extension ratio (T/C %) expressed by the above-mentioned equation assuming the survival period of the control group as 100%. The results obtained are shown in Table 14. The measurement of the survival period was limited up until 51 days from the transplantation.

In order to confirm the effect of the administration of the test substances, the changes in body weight and feed uptake amount of mice measured throughout the 10 days before the transplantation of Leukemia L-1210 and all animal survival period after the transplantation (12 days after the transplantation) are shown in Tables 15 and 16, respectively.

TABLE 14

Life Extension Effect

| Classification | | Average number of days of survival | Life extension ratio (%) | Number of surviving * |
|---|---|---|---|---|
| Control group | | 14 | 100 | 0 |
| I-01A (2): I-01B-administered group | 35% feed mixing ratio | 22 | 157.1 | 0 |
| | 45% feed mixing ratio | 26 | 185.7 | 2 |
| I-01A (2): I-01C-administered group | 25% feed mixing ratio | 30 | 214.3 | 3 |
| | 35% feed mixing ratio | 27 | 192.9 | 1 |
| I-01B:I-01C-administered group | 20% feed mixing ratio | 19 | 135.7 | 0 |
| | 30% feed mixing ratio | 22 | 157.1 | 1 |
| I-01A (2): I-01B: I-01C-administered group | 25% feed mixing ratio | 23 | 164.3 | 1 |
| | 33% feed mixing ratio | 32 | 228.6 | 3 |
| | 40% feed mixing ratio | 22 | 157.1 | 0 |

* Number of those surviving at the end of the period.

TABLE 15-1

Changes in Body Weight

| Classification | | Day of measurement | | | |
|---|---|---|---|---|---|
| | | Day 1 | Day 4 | Day 7 | Day 11* |
| Control group | | 22.2 ± 1.2 | 22.7 ± 1.2 | 23.3 ± 1.1 | 24.3 ± 1.3 |
| I-01A (2):I-01B-administered group | 35% feed mixing ratio | 22.0 ± 1.1 | 22.1 ± 1.2 | 23.1 ± 1.3 | 24.4 ± 0.9 |
| | 45% feed mixing ratio | 22.0 ± 1.0 | 22.1 ± 1.0 | 22.9 ± 1.2 | 23.0 ± 1.0 |
| I-01A (2):I-01C-administered group | 25% feed mixing ratio | 21.9 ± 1.1 | 22.2 ± 1.1 | 22.9 ± 1.1 | 23.5 ± 1.2 |
| | 35% feed mixing ratio | 22.3 ± 1.1 | 22.9 ± 1.2 | 23.6 ± 1.1 | 24.1 ± 1.1 |
| I-01B:I-01C-administered group | 20% feed mixing ratio | 21.9 ± 1.4 | 20.9 ± 2.2 | 22.4 ± 1.9 | 23.0 ± 3.2 |
| | 30% feed mixing ratio | 22.4 ± 1.2 | 21.1 ± 1.8 | 22.0 ± 3.0 | 22.8 ± 2.1 |
| I-01A (2):I-01B: I-01C-administered group | 25% feed mixing ratio | 22.4 ± 1.2 | 22.3 ± 1.1 | 23.3 ± 1.7 | 24.3 ± 1.3 |
| | 33% feed mixing ratio | 22.1 ± 1.0 | 21.8 ± 1.2 | 22.4 ± 1.2 | 23.7 ± 1.4 |
| | 40% feed mixing ratio | 22.2 ± 1.5 | 22.3 ± 1.3 | 22.9 ± 1.3 | 23.4 ± 1.9 |

The values are shown as average value ± standard deviation and the days of measurement were reckoned from the starting day of the administration of the test substances.
*L-1210 administration day

TABLE 15-2

Changes in Body Weight

| Classification | | Day of measurement | | | |
|---|---|---|---|---|---|
| | | Day 14 | Day 17 | Day 20** | Day 23 |
| Control group | | 24.6 ± 1.4 | 25.5 ± 1.4 | 28.3 ± 2.0 | 28.5 ± 2.8 |
| I-01A (2):I-01B-administered group | 35% feed mixing ratio | 24.7 ± 1.1 | 25.3 ± 1.4 | 27.8 ± 1.3 | 29.0 ± 2.3 |
| | 45% feed mixing ratio | 23.6 ± 1.2 | 24.2 ± 1.4 | 26.7 ± 1.5 | 29.1 ± 3.1 |
| I-01A (2):I-01C-administered group | 25% feed mixing ratio | 23.9 ± 1.1 | 24.8 ± 1.4 | 27.6 ± 1.6 | 28.6 ± 3.2 |
| | 35% feed mixing ratio | 24.6 ± 1.1 | 25.2 ± 1.2 | 28.3 ± 1.4 | 28.8 ± 2.4 |
| I-01B:I-01C-administered group | 20% feed mixing ratio | 23.3 ± 3.5 | 24.2 ± 3.1 | 27.5 ± 3.3 | 26.7 ± 4.4 |
| | 30% feed mixing ratio | 24.0 ± 1.5 | 24.4 ± 1.4 | 27.7 ± 1.9 | 27.2 ± 3.0 |
| I-01A (2):I-01B: I-01C administered group | 25% feed mixing ratio | 24.5 ± 1.8 | 25.9 ± 1.4 | 29.5 ± 2.5 | 26.8 ± 2.6 |
| | 33% feed mixing ratio | 23.9 ± 1.1 | 24.7 ± 1.2 | 27.2 ± 1.6 | 27.8 ± 2.6 |
| | 40% feed mixing ratio | 23.9 ± 1.9 | 24.6 ± 1.6 | 27.7 ± 3.3 | 28.2 ± 3.5 |

The values are shown as average value ± standard deviation and the days of measurement were reckoned from the starting day of the administration of the test substances.
**As a result of abdominal bloating due to disease exacerbation, body weight increased suddenly.

TABLE 16-1

Changes in Feed Uptake Amount

| Classification | | Day of measurement | | | |
|---|---|---|---|---|---|
| | | Day 1–4 | Day 4–7 | Day 7–11 | Day 11–14 |
| Control group | | 3.9 ± 0.3 | 4.0 ± 0.2 | 3.9 ± 0.3 | 3.7 ± 0.3 |
| I-01A (2):I-01B-administered group | 35% feed mixing ratio | 3.8 ± 0.3 | 4.1 ± 0.4 | 4.2 ± 0.2 | 4.0 ± 0.3 |
| | 45% feed mixing ratio | 3.6 ± 0.3 | 4.1 ± 0.3 | 3.8 ± 0.5 | 4.2 ± 0.5 |
| I-01A (2):I-01C-administered group | 25% feed mixing ratio | 3.7 ± 0.4 | 4.0 ± 0.5 | 3.9 ± 0.3 | 3.8 ± 0.4 |
| | 35% feed mixing ratio | 4.0 ± 0.6 | 4.3 ± 0.3 | 4.3 ± 0.3 | 4.0 ± 0.5 |
| I-01B:I-01C-administered group | 20% feed mixing ratio | 3.4 ± 0.6 | 4.4 ± 0.2 | 4.3 ± 0.8 | 4.4 ± 0.4 |
| | 30% feed mixing ratio | 2.7 ± 0.9 | 4.1 ± 1.1 | 4.3 ± 0.4 | 4.4 ± 0.3 |
| I-01A (2):I-01B: I-01C-administered group | 25% feed mixing ratio | 3.7 ± 0.4 | 4.3 ± 0.5 | 4.3 ± 0.2 | 4.1 ± 0.8 |
| | 33% feed mixing ratio | 3.7 ± 0.5 | 4.3 ± 0.5 | 4.2 ± 0.5 | 4.2 ± 0.4 |
| | 40% feed mixing ratio | 3.7 ± 0.3 | 4.2 ± 0.5 | 3.7 ± 0.5 | 4.2 ± 0.5 |

The values are shown as average value ± standard deviation and the days of measurement were reckoned from the starting day of the administration of the test substances.

TABLE 16-2

Changes in Feed Uptake Amount

| Classification | | Day 14–17 | Day 17–20 | Day 20–23 |
|---|---|---|---|---|
| Control group | | 4.2 ± 0.4 | 3.3 ± 0.4 | 1.5 ± 0.6 |
| I-01A (2):I-01B- administered group | 35% feed mixing ratio | 4.0 ± 0.4 | 4.0 ± 0.8 | 3.3 ± 0.7 |
| | 45% feed mixing ratio | 4.1 ± 0.4 | 4.3 ± 0.7 | 3.2 ± 0.7 |
| I-01A (2):I-01C- administered group | 25% feed mixing ratio | 4.1 ± 0.5 | 3.9 ± 0.4 | 2.8 ± 1.0 |
| | 35% feed mixing ratio | 3.9 ± 0.4 | 3.8 ± 0.2 | 3.1 ± 0.6 |
| I-01B:I-01C- administered group | 20% feed mixing ratio | 4.4 ± 0.2 | 4.2 ± 0.5 | 2.8 ± 1.2 |
| | 30% feed mixing ratio | 4.3 ± 0.3 | 4.3 ± 0.3 | 2.7 ± 1.0 |
| I-01A (2):I-01B: I-01C- administered group | 25% feed mixing ratio | 4.1 ± 0.4 | 4.1 ± 0.6 | 2.3 ± 1.2 |
| | 33% feed mixing ratio | 4.0 ± 0.2 | 4.5 ± 1.1 | 3.3 ± 0.9 |
| | 40% feed mixing ratio | 4.1 ± 0.5 | 4.1 ± 0.6 | 3.3 ± 0.7 |

The values are shown as average value ± standard deviation and the days of measurement were reckoned from the starting day of the administration of the test substances.

Example 3

Example 2 was repeated except that instead of the composition of I-01A(2):I-01B:I-01C=65:35:3 (weight ratio), a composition of I-01A(1):I-01B:I-01C=65:35:3 (weight ratio) was used. As a result, anticancer effect against ascites tumor was observed in the same manner as in Example 2. In particular, at a mixing ratio of 30%, the highest life extension ratio was obtained. Also, similar results were obtained on the tests on changes in body weight and feed uptake amount.

What is claimed is:

1. A composition having an anticancer activity, comprising therapeutically effective amounts of
   a dry product of *Angelica keiskei* and/or a roasted dry product of *Camellia japonica*, and
   a dry product of defatted whole egg of eggs of a fowl bred by feeding a feed having blended therein an additive comprising a dry product of *Angelica keiskei*, a dry product of brown algae, and optionally a roasted dry product of *Camellia japonica*.

2. The composition according to claim 1, wherein the fowl is a member selected from the group consisting of hens, ducks and quails.

3. The composition according to claim 1, wherein the roasted dry product is obtained by a roasting process comprising roasting with a hot iron plate drum roasting apparatus at 100° to 150° C. for 10 to 30 minutes.

4. The composition according to claim 1, wherein the defatted whole egg and the dry products of *Angelica keiskei* or *Camellia japonica* are present in a weight ratio of 1-10:0.5-5.

5. The composition according to claim 1, wherein the defatted whole egg and the dry products of *Angelica keiskei* and *Camellia japonica* are present in said composition in a weight ratio of 1-10:0.5-5:0.5-5.

6. The composition according to claim 1, which is in the form of at least one selected from the group consisting of capsule, granule, and tablet.

7. The composition according to claim 1, wherein the defatted whole egg and the dry products of *Angelica keiskei* and *Camellia japonica* are present in said composition in a weight ratio of 1-2:0.5-1:0.5-1.

8. A composition having an anticancer activity, comprising therapeutically effective amounts of a dry product of *Angelica keiskei* and a roasted dry product of *Camellia japonica*.

9. The composition according to claim 8, wherein the roasted dry product is obtained by a roasting process comprising roasting with a hot iron plate drum roasting apparatus at 100° to 150° C. for 10 to 30 minutes.

10. The composition according to claim 8, wherein the dry products of *Angelica keiskei* and *Camellia japonica* are present in said composition in a weight ratio of 1-10:1-10.

11. The composition according to claim 8, wherein the dry products of *Angelica keiskei* and *Camellia japonica* are present in said composition in a weight ratio of 1-2:1-2.

12. The composition according to claim 8, which is in the form of at least one selected from the group consisting of capsule, granule, and tablet.

* * * * *